United States Patent
Kawata et al.

(10) Patent No.: US 11,992,305 B2
(45) Date of Patent: May 28, 2024

(54) MAGNETIC RESONANCE IMAGING APPARATUS THAT DEFORMS A MORPHOLOGY IMAGE TO COINCIDE WITH A FUNCTION IMAGE, IMAGE PROCESSING APPARATUS, AND IMAGE PROCESSING METHOD

(71) Applicant: Hitachi, Ltd., Tokyo (JP)

(72) Inventors: Yasuo Kawata, Tokyo (JP); Masahiro Takizawa, Tokyo (JP); Nobuyuki Yoshizawa, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 0 days.

(21) Appl. No.: 17/230,046

(22) Filed: Apr. 14, 2021

(65) Prior Publication Data

US 2022/0061691 A1 Mar. 3, 2022

(30) Foreign Application Priority Data

Aug. 31, 2020 (JP) .................... 2020-145298

(51) Int. Cl.
*A61B 5/00* (2006.01)
*A61B 5/055* (2006.01)
(Continued)

(52) U.S. Cl.
CPC ............ *A61B 5/055* (2013.01); *A61B 5/0042* (2013.01); *G01R 33/50* (2013.01); *G01R 33/5608* (2013.01); *G01R 33/56308* (2013.01)

(58) Field of Classification Search
CPC ...... A61B 5/055; A61B 5/0042; G01R 33/50; G01R 33/5608; G01R 33/56308; G01R 33/5602; G01R 33/56366; G01R 33/4822
See application file for complete search history.

(56) References Cited

U.S. PATENT DOCUMENTS

2008/0119721 A1* 5/2008 Kimura ................. A61B 5/055
600/410
2009/0253984 A1* 10/2009 Yui ........................ A61B 5/055
600/420

(Continued)

FOREIGN PATENT DOCUMENTS

JP 2006-119022 A 5/2006
JP 2013198763 A 10/2013
(Continued)

OTHER PUBLICATIONS

Tsujikawa T, Kimura H, Matsuda T, Fujiwara Y, Isozaki M, Kikuta K-i, et al. (2016) Arterial Transit Time Mapping Obtained by Pulsed Continuous 3D Asl Imaging with Multiple Post-Label Delay Acquisitions: Comparative Study with PET-CBF in Patients with Chronic Occlusive Cerebrovascular Disease. PLoS ON (Year: 2016).*
(Continued)

*Primary Examiner* — Serkan Akar
*Assistant Examiner* — Gabriel Victor Popescu
(74) *Attorney, Agent, or Firm* — MATTINGLY & MALUR, PC

(57) ABSTRACT

A magnetic resonance imaging apparatus captures a morphology image and a function image that are captured with respect to an equal imaging region of an object under examination. Processing for deforming the morphology image is performed using a deformation parameter and moving positions of structural objects included in the morphology image to respective positions of structural objects of a previously determined standard morphology. Then, the function image is deformed using a value of the deformation parameter used in deforming the morphology image to cause a position of a region included in the function image to coincide with a position of a corresponding region of the standard morphology or by using the standard morphology in an opposite direction using the value of the deformation (Continued)

parameter to cause a position of a region of the structural object thereof to coincide with a position of a corresponding region included in the function image.

12 Claims, 11 Drawing Sheets

(51) Int. Cl.
*G01R 33/50* (2006.01)
*G01R 33/56* (2006.01)
*G01R 33/563* (2006.01)

(56) References Cited

U.S. PATENT DOCUMENTS

2018/0321347 A1* 11/2018 Wang ............... A61B 5/055
2018/0338701 A1* 11/2018 Amemiya ......... A61B 5/055

FOREIGN PATENT DOCUMENTS

| JP | 2013-255586 A | 12/2013 |
| JP | 2014104097 A | 6/2014 |
| JP | 2015-91308 A | 5/2015 |
| JP | 2020010972 A | 1/2020 |

OTHER PUBLICATIONS

Hirohiko Kimura, et al., "Cerebral perfusion measurements using continuous arterial spin labeling: accuracy and limits of a quantitative approach", International Congress Series 1265: 236-247 (2004).

Japanese Office Action received in corresponding Japanese Application No. 2020-145298 dated Dec. 12, 2023.

Japanese Office Action received in corresponding Japanese Application No. 2020-145298 dated Apr. 9, 2024.

* cited by examiner

FIG. 4

| Scan parameter | | | | | |
|---|---|---|---|---|---|
| FOV | 240mm | TR | 4750ms | Slice# | 48 |
| Matrix (UNIT OF SIGNAL ACQUISITION) | 48×48(3T) 32×32(1.5T) | TE | 15.2ms | Thickness | 3mm |
| PLD | 500, 750, 1000, 1500, 2000, 2500, 3000ms | | | Total Time | 8min20s |

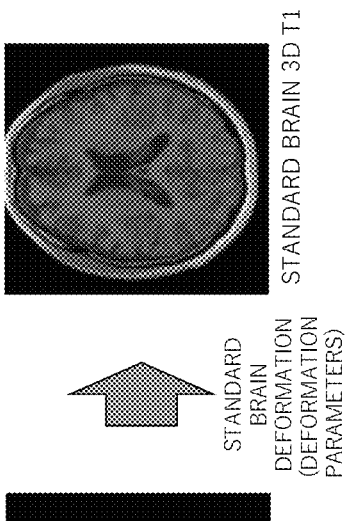
FIG. 5A1
ANATOMICAL STANDARDIZATION OF 3D T1-WEIGHTED IMAGE
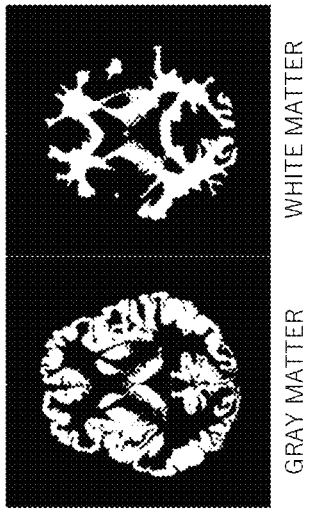
FIG. 5A2
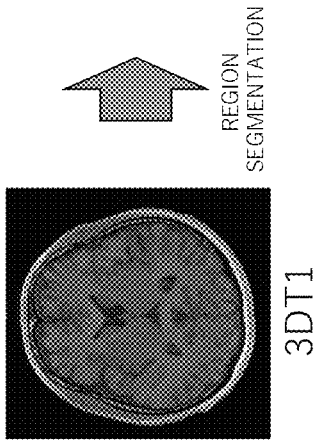
FIG. 5B1
ANATOMICAL STANDARDIZATION OF CBF IMAGE AND ATT IMAGE
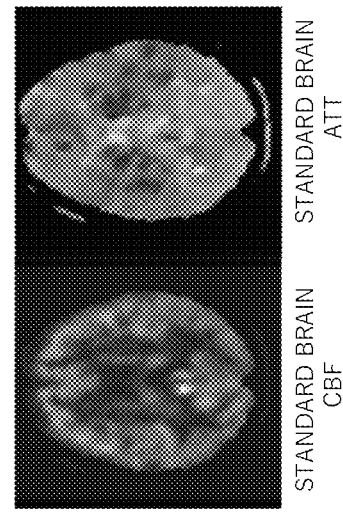
FIG. 5A3
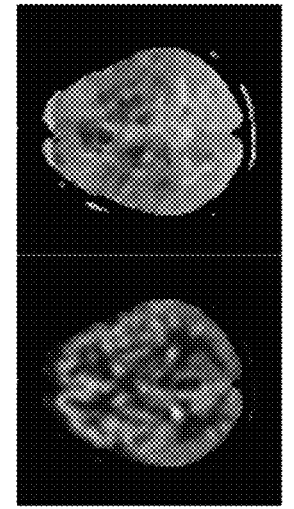
FIG. 5B2

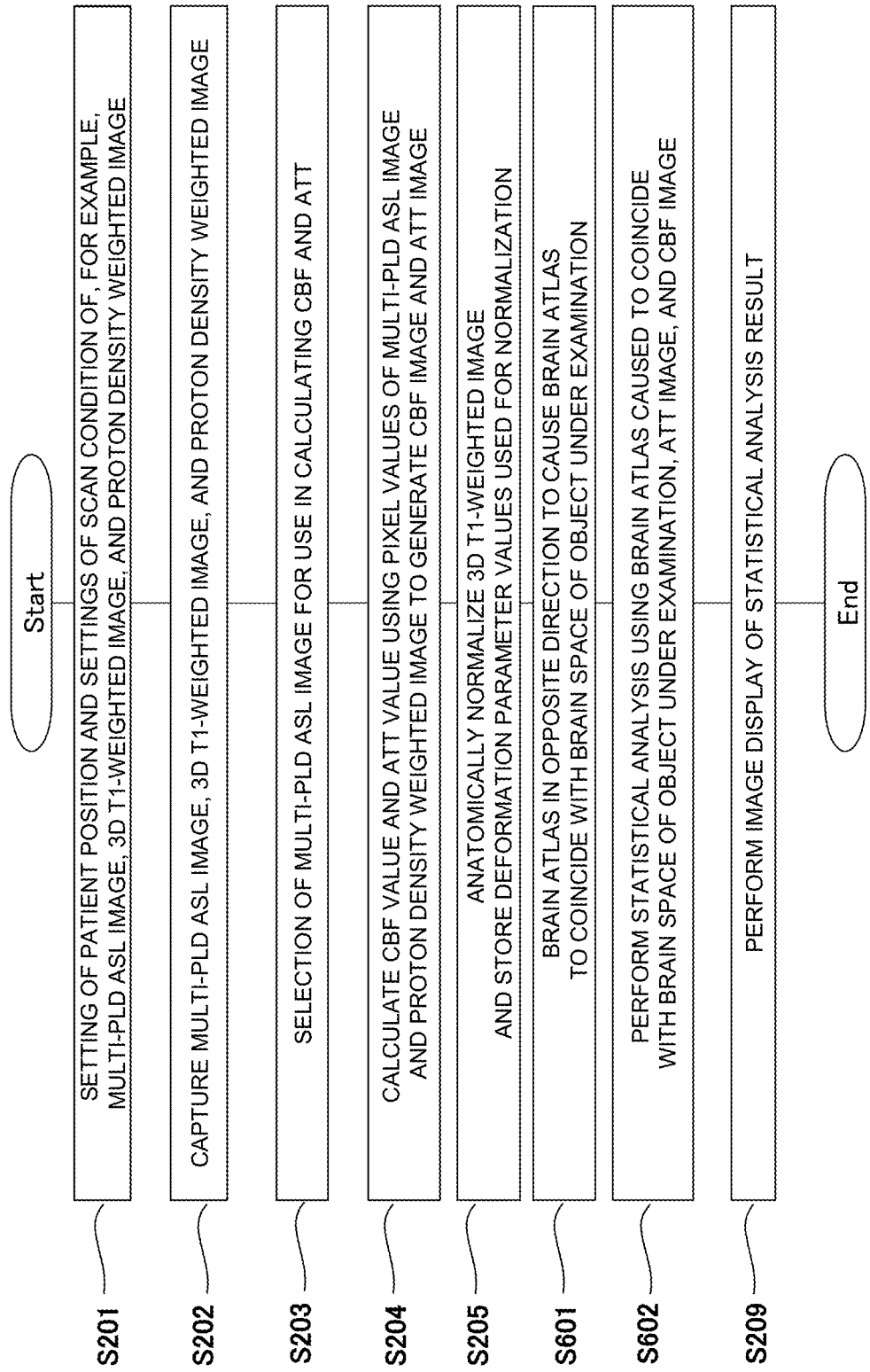

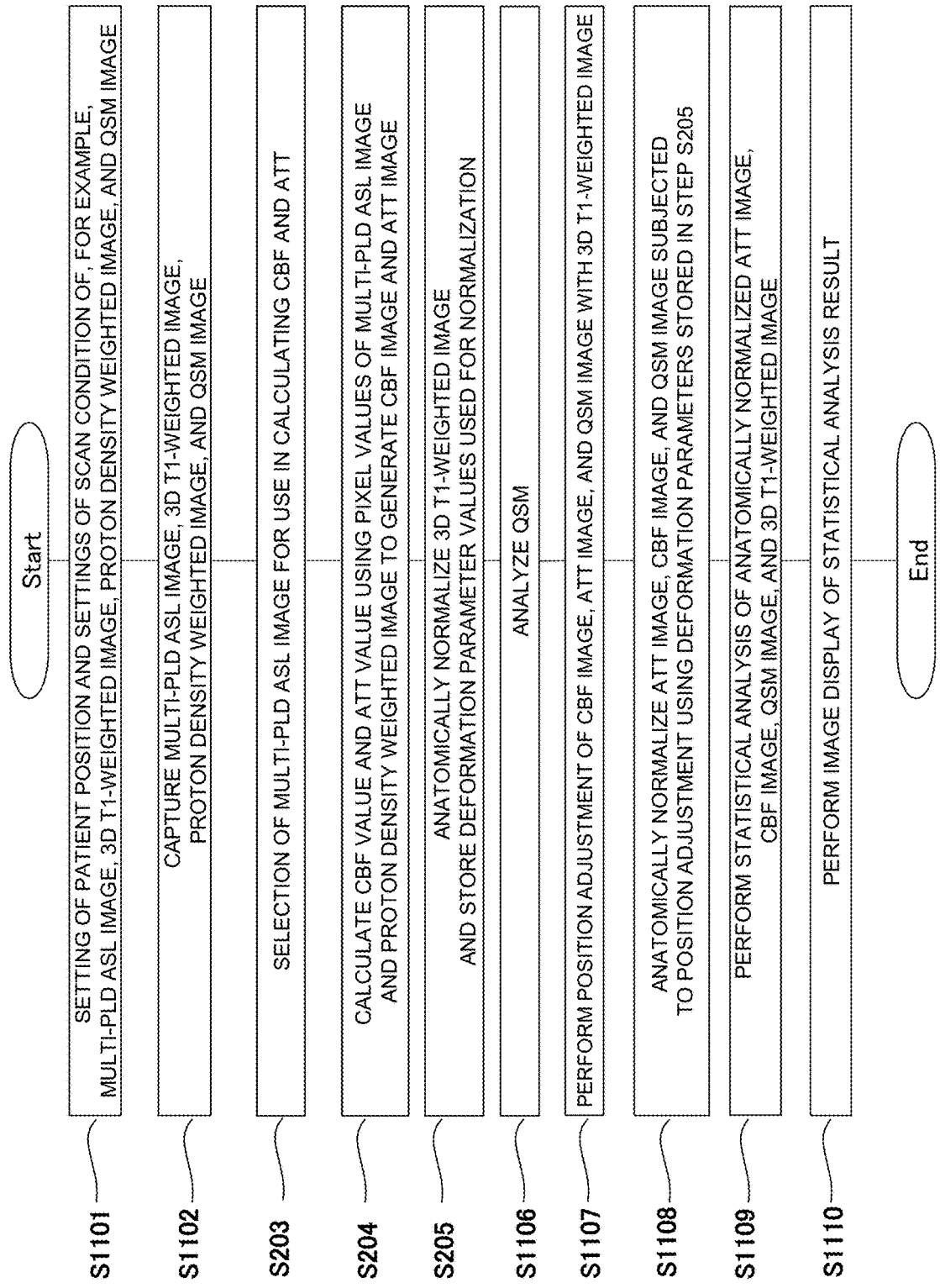

MAGNETIC RESONANCE IMAGING APPARATUS THAT DEFORMS A MORPHOLOGY IMAGE TO COINCIDE WITH A FUNCTION IMAGE, IMAGE PROCESSING APPARATUS, AND IMAGE PROCESSING METHOD

CROSS-REFERENCE TO RELATED APPLICATION

The present application claims priority from Japanese application JP2020-145298, filed on Aug. 31, 2020, the contents of which is hereby incorporated by reference into this application.

BACKGROUND OF THE INVENTION

Field of the invention

The present invention relates to a magnetic resonance imaging (hereinafter referred to as "MRI") apparatus, an image processing apparatus, and an image processing method and, more particularly relates to a technique to analyze cerebral hemodynamics based on a blood flow image.

Description of the Related Art

The MRI apparatus is an apparatus which measures a nuclear magnetic resonance (NMR) signal generated by nuclear spins configuring an object under examination, particularly, an organ in the human body and performs two-dimensional or three-dimensional imaging of the morphology or function of, for example, the head region, abdominal region, or extremities of the human body. At the time of imaging, the NMR signal is subjected to addition of a phase encode which varies with a gradient magnetic field and is concurrently frequency-encoded, thus being measured as time-series data. The measured NMR signal is reconstructed into an image by being two-dimensionally or three-dimensionally Fourier transformed.

Diagnostic imaging of cerebral vascular diseases such as dementia, cerebral infarction, and angiostenosis, and brain diseases such as epilepsy in which disorder of cerebral blood flow is found is being performed by evaluating cerebral hemodynamics.

Imaging methods for cerebral blood flow using MRI include an arterial spin labeling (ASL) method (see Non-Patent Literature 1). The ASL method radiates a radiofrequency (RF) pulse onto a label plane set on the more upstream side of a blood flow than an image capturing region and thus inverts the spins of protons of blood which passes through the label plane (labeling). When the blood the spins of protons of which have been inverted arrives at the image capturing region through the blood stream, the blood proton spins are replaced by spins of protons in tissues included in the image capturing region at capillaries, so that the spin-lattice (T1) relaxation time of the tissues changes. Finding a difference between a label image obtained by imaging an image capturing region set in that state and a control image obtained by imaging the blood protons without inverting the blood protons enables acquiring a blood flow image. This method is able to perform labeling of blood with an RF pulse and is, therefore, able to generate a blood flow image in a non-invasive manner.

On the other hand, there is known a method called anatomic standardization (normalization) which converts a brain image of a subject obtained by, for example, positron emission tomography (PET) or MRI into a standard brain coordinate system to coordinate with a standard brain. Using this anatomic standardization to convert a brain image which is morphologically different with each person into a standard brain enables comparing images of blood flow or metabolism between subjects on a pixel-by-pixel basis or comparing such images between subject groups. Known methods for anatomic standardization include, for example, diffeomorphic anatomical registration through exponentiated Lie algebra (DARTEL) processing, which performs non-linear conversion using a large number of parameters.

Moreover, Patent Literature 1 discloses a technique to obtain a cerebral blood flow image using single photon emission computed tomography (SPECT), which, following the administration of a medicine labeled by a radioisotope to an object under examination, detects released radiation to obtain projection data and performs image reconstruction using the project data. The technique disclosed in Patent Literature 1 obtains a standard brain image by deforming a reconstructed image in conformity with a standard brain (anatomical normalization) and performs quantification on the standard brain image to obtain various types of quantitative value images. Moreover, there is proposed a method which performs evaluation of hemodynamics using the obtained quantitative value images to perform, for example, pathological condition analysis using quantitative evaluation.

LIST OF RELATED ART

Non-Patent Literature

Non-Patent Literature 1: Kimura, Kabasawa, Yonekura, et al., Cerebral perfusion measurements using continuous arterial spin labeling: accuracy and limits of a quantitative approach, International Congress Series, 1256: 236-247, 2004

Patent Literature

Patent Literature 1: JP-A-2006-119022

SUMMARY OF THE INVENTION

The ASL method, which captures a cerebral blood flow image using an MRI apparatus, is able to perform imaging in a non-invasive manner without the need to use a medicine and is, therefore, advantageous for objects under examination as compared with SPECT. Moreover, since, if it is possible to convert a cerebral blood flow image obtained by the ASL method into a standard brain coordinate system, it is possible to compare respective blood flows of an object under examination and a healthy subject using the same coordinate system, the MRI apparatus is useful for, for example, diagnosis.

However, since a cerebral blood flow image captured by the ASL method does not include shape information about a brain, it is difficult to accurately convert a cerebral blood flow image into a standard brain coordinate system.

While Patent Literature 1 discloses obtaining deformation parameters for deforming a cerebral blood flow image obtained by SPECT in such a way as to coordinate with a standard brain, since a cerebral blood flow image obtained by SPECT also does not include shape information, it is presumed that it is not actually easy to accurately perform coordinate conversion in conformity with a standard brain.

Moreover, the technique which obtains a cerebral blood flow image using SPECT described in Patent Literature 1 requires a longer examination time and a higher examination cost as compared with the case of performing imaging using an MRI apparatus as described in Non-Patent Literature 1.

Aspects of the present invention are directed to performing anatomical normalization which causes a function image such a blood flow image obtained by using an MRI apparatus to accurately coincide with a standard morphology.

According to an aspect of the present invention, a magnetic resonance imaging apparatus includes a static magnetic field generation unit that applies a static magnetic field to an imaging space in which an object under examination is placed, a gradient magnetic field generation unit that applies a gradient magnetic field to the imaging space, an irradiation coil that irradiates the object under examination in the imaging space with a high-frequency magnetic field, a receiving coil that receives a nuclear magnetic resonance signal from the object under examination, a measurement control unit that performs an imaging sequence by controlling the gradient magnetic field generation unit, the irradiation coil, and the receiving coil to capture an image, and a computation processing unit. The measurement control unit captures, with respect to an equal imaging region of the object under examination, a morphology image with a morphology expressed therein and a function image with a function expressed therein. After performing processing for deforming the morphology image using a deformation parameter and moving positions of one or more structural objects included in the morphology image to respective positions of structural objects of a previously determined standard morphology, the computation processing unit deforms the function image using a value of the deformation parameter used in deforming the morphology image to cause a position of a region included in the function image to coincide with a position of a corresponding region of the standard morphology or deforms the standard morphology in an opposite direction using the value of the deformation parameter to cause a position of a region of the structural object of the standard morphology to coincide with a position of a corresponding region included in the function image.

According to an embodiment of the present invention, since it is possible to perform anatomical normalization which causes a function image such a blood flow image obtained by using an MRI apparatus to accurately coincide with a standard morphology, it is possible to readily evaluate the obtained function image while comparing it with a function image of a healthy subject.

BRIEF DESCRIPTION OF THE DRAWINGS

FIG. 4 is a diagram illustrating an example of a scan condition of the imaging pulse sequence illustrated in FIG. 2.

FIGS. 5A1, 5A2, and 5A3 are explanatory diagrams illustrating a procedure for anatomical normalization of a 3D T1-weighted image, and FIGS. 5B1 and 5B2 are explanatory diagrams illustrating a procedure for anatomical normalization of a CBF image and an ATT image.

FIG. 10 is a flowchart illustrating a processing flow of the computation processing unit 8 of an MRI apparatus in a fifth embodiment.

FIG. 11 is a flowchart illustrating a processing flow of the computation processing unit 8 of an MRI apparatus in a sixth embodiment.

DESCRIPTION OF THE EMBODIMENTS

Figure 1:
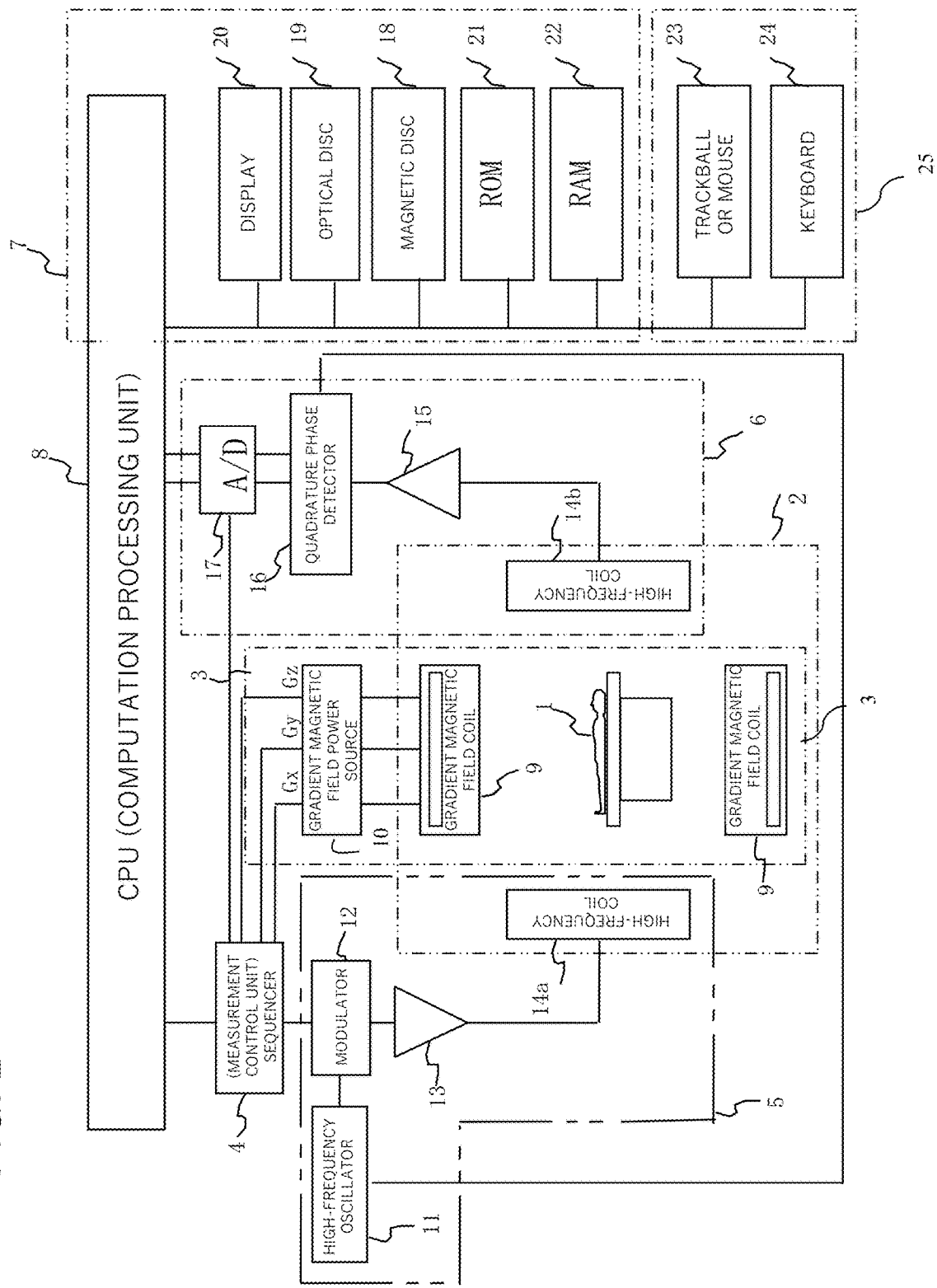
FIG. 1 is a block diagram illustrating an example of an overall configuration of an MRI apparatus in a first embodiment of the present invention.

Various embodiments of an MRI apparatus in the present invention are described below in detail with reference to the accompanying drawings. Furthermore, in all of the figures used to describe embodiments of the present invention, elements having the respective same functions are assigned the respective same reference numerals and any repetitive descriptions thereof are omitted.

First Embodiment

First, an outline of an MRI apparatus in a first embodiment is described.

The MRI apparatus in the first embodiment has, for example, a configuration illustrated in FIG. 1, and includes a static magnetic field generation unit 2, which applies a static magnetic field to an imaging space in which an object under examination 1 is placed, a gradient magnetic field generation unit 3, which applies a gradient magnetic field to the imaging space, an irradiation coil 14a, which irradiates the object under examination 1 in the imaging space with a high-frequency magnetic field, a receiving coil 14b, which receives a nuclear magnetic resonance signal from the object under examination 1, a measurement control unit (sequencer) 4, which performs an imaging sequence by controlling the gradient magnetic field generation unit 3, the irradiation coil 14a, and the receiving coil 14b to capture an image, and a computation processing unit 8.

The measurement control unit 4 captures, with respect to the same imaging region of the object under examination 1, a morphology image with a morphology expressed therein and a function image with a function expressed therein.

The computation processing unit 8 performs processing for deforming the morphology image using a deformation parameter and moving positions of one or more structural objects included in the morphology image to respective positions of structural objects of a previously determined standard morphology (anatomical normalization processing). The computation processing unit 8 deforms the function image using a value of the deformation parameter used in deforming the morphology image to cause a position of a region included in the function image to coincide with a position of a corresponding region of the standard morphology.

Alternatively, the computation processing unit 8 deforms the standard morphology in an opposite direction using the value of the deformation parameter to cause a position of a region of the structural object of the standard morphology to coincide with a position of a corresponding region included in the function image.

This enables performing anatomical normalization which causes coordinates of a function image with the morphology of a brain not expressed therein, such as a blood flow image obtained by using the MRI apparatus, to accurately coincide with coordinates of a standard morphology. Accordingly, since it is possible to compare function images, such as blood flow images, of the object under examination 1 and a healthy subject using the same coordinate system, the MRI apparatus is useful for, for example, diagnosis.

The morphology image as mentioned herein is an image with the morphology of an object under examination expressed therein, and, here, a T1-weighted image is used as the morphology image. Furthermore, the morphology image is not limited to a T1-weighted image, and, as long as being an image with the morphology of an object under examination expressed therein, the morphology image can be another image such as an absolute value image, a T2-weighted image, or a proton density weighted image.

The function image is an image with the function of an object under examination expressed therein. In the present embodiment, an example in which the function image is an arterial spin labeling (ASL) image, which is a cerebral blood flow image, particularly, an arterial blood flow arrival time (arterial transit time (ATT)) image, which is calculated from a multi-PLD ASL image, and/or a cerebral blood flow (CBF) image, is described. Furthermore, the function image is not limited to these images, and, as long as being an image with the function of an object under examination expressed therein, the function image can be, for example, an image with various physical property values or quantitative values, such as T2, T2*, diffusion coefficient, flow rate, magnetic susceptibility, elastic modulus, and concentration of contrast medium, set as pixels values, or a fluid attenuated inversion recovery (FLAIR) image with a signal of water attenuated.

On the other hand, the standard morphology can be any morphology as long as being a morphology with coordinates of one or more structural objects determined. For example, a standard brain of Talairach can be used as the standard morphology.

In this way, the present embodiment does not directly normalize a function image such as a cerebral blood flow image with respect to a standard morphology (for example, a standard brain), but first deforms a morphology image obtained by imaging the same imaging region to cause coordinates of the morphology image to coincide with coordinates of a structural object of a standard morphology (for example, a standard brain) (normalization) and then deforms the function image using a value of the deformation parameter used in deforming the morphology image, thus being able to accurately normalize the function image even in a case where the function image does not include morphology information.

Furthermore, while it is favorable that the morphology image is an image obtained by imaging the same imaging region following imaging of the function image, the morphology image can be an image obtained by imaging performed before or after imaging of the function image as long as being an image obtained by imaging the same imaging region of the same object under examination.

<Configuration of MRI Apparatus>

The MRI apparatus in the present embodiment is described below in detail.

A structure of the MRI apparatus in the present embodiment is described in detail with reference to FIG. 1. FIG. 1 is a block diagram illustrating an overall configuration of an embodiment of the MRI apparatus according to the present invention. The MRI apparatus is an apparatus which obtains a tomographic image of an object under examination using an NMR phenomenon, and, as illustrated in FIG. 1, the MRI apparatus is configured to include a static magnetic field generation system (static magnetic field generation unit) 2, a gradient magnetic field generation system (gradient magnetic field generation unit) 3, a transmission system 5, a reception system 6, a signal processing system 7, a sequencer (measurement control unit) 4, and a central processing unit (CPU) (computation processing unit) 8.

The static magnetic field generation system 2 applies a static magnetic field to an imaging space in which an object under examination is placed. If the static magnetic field generation system 2 is of the vertical magnetic field type, the static magnetic field generation system 2 generates a homogeneous static magnetic field in a direction perpendicular to the body axis of the object under examination 1, and, if the static magnetic field generation system 2 is of the horizontal magnetic field type, the static magnetic field generation system 2 generates a homogeneous static magnetic field in the direction of the body axis of the object under examination 1. A static magnetic field generation source of the permanent magnet type, the normal conduction type, or the superconduction type is arranged around the object under examination 1.

The gradient magnetic field generation system 3 applies a gradient magnetic field to the imaging space. The gradient magnetic field generation system. 3 includes gradient magnetic field coils 9, which apply gradient magnetic fields in the directions of three axes, i.e., X-, Y-, and Z-axes, in the coordinate system (coordinate system at rest) of the MRI apparatus, and a gradient magnetic field power source 10, which drives the respective gradient magnetic field coils 9. The gradient magnetic field generation system 3 drives the gradient magnetic field power source 10 for the respective gradient magnetic field coils 9 according to instructions from the sequencer 4 described below, and thus applies gradient magnetic fields Gx, Gy, and Gz in the directions of three axes, i.e., X-, Y-, and Z-axes. At the time of imaging, the gradient magnetic field generation system 3 applies a slice selection gradient magnetic field (Gs) in a direction perpendicular to a slice plane (imaging cross section) to set the slice plane with respect to the object under examination 1, and applies a phase encode gradient magnetic field pulse (Gp) and a frequency encode gradient magnetic field pulse (Gf) in the remaining two directions perpendicular to the slice plane and perpendicular to each other to encode position information about the respective directions into an echo signal.

The sequencer 4 controls the gradient magnetic field generation system 3, the transmission system 5, and the reception system 6 to perform an imaging sequence, thus capturing an image. Specifically, the sequencer 4 is a control unit which repeatedly applies a high-frequency magnetic field pulse (hereinafter referred to as an "RF pulse") and a gradient magnetic field pulse in a predetermined pulse sequence, operates under the control of the computation processing unit 8, and transmits various instructions required for data acquisition of a tomographic image of the object under examination 1 to the transmission system 5, the gradient magnetic field generation system 3, and the reception system 6.

The transmission system 5 is a system which irradiates the object under examination 1 with an RF pulse (high-frequency magnetic field) to cause nuclear magnetic resonance to occur in nuclear spins of atoms constituting body tissues of the object under examination 1, and includes a high-frequency oscillator 11, a modulator 12, a high-frequency amplifier 13, and a transmitting-side high-frequency coil (transmitting coil) 14a. An RF pulse output from the high-frequency oscillator 11 is amplitude-modulated by the modulator 12 at timing indicated by an instruction from the sequencer 4, and the amplitude-modulate RF pulse is amplified by the high-frequency amplifier 13 and is then supplied to the high-frequency coil 14a, which is arranged in proximity to the object under examination 1, so that the object under examination 1 is irradiated with the RF pulse.

The reception system 6 is a system which receives an echo signal (NMR signal) released by nuclear magnetic resonance of nuclear spins of atoms constituting body tissues of the object under examination 1, and includes a receiving-side high-frequency coil (receiving coil) 14b, a signal amplifier 15, a quadrature phase detector 16, and an analog-digital (A/D) converter 17. An NMR signal representing a response of the object under examination 1 induced by electromagnetic waves radiated from the transmitting-side high-frequency coil 14a is detected by the high-frequency coil 14b, which is arranged in proximity to the object under examination 1, is amplified by the signal amplifier 15, and is then divided into two channel signals, which are orthogonal, by the quadrature phase detector 16 at timing indicated by an instruction from the sequencer 4, so that the two channel signals are converted into respective digital quantities by the A/D converter 17 and are then transmitted to the signal processing system 7.

The signal processing system 7 is a system which performs, for example, various data processing operations and displaying and storing of processing results. The signal processing system 7 includes external storage devices, such as an optical disc 19 and a magnetic disc 18, and a display 20, which is configured with, for example, a cathode-ray tube (CRT).

The computation processing unit (CPU) 8 receives data from the reception system 6 and performs predetermined signal processing on the received data, and then performs image reconstruction processing to generate a tomographic image of the object under examination 1. The generated image is displayed on the display 20 and is concurrently recorded on, for example, the magnetic disc 18, which is an external storage device.

An operation unit 25 is a unit via which to input various pieces of control information for the MRI apparatus and control information for processing which is performed by the signal processing system 7, and includes a trackball or mouse 23 and a keyboard 24. The operation unit 25 is arranged in proximity to the display 20, and the operator interactively controls various processing operations of the MRI apparatus via the operation unit 25 while viewing the display 20.

Furthermore, as illustrated in FIG. 1, the transmitting-side high-frequency coil 14a and the gradient magnetic field coils 9 are arranged within a static magnetic field space of the static magnetic field generation system 2, into which the object under examination 1 is inserted, in such a way as to face the object under examination 1 if the static magnetic field generation system 2 is of the vertical magnetic field type or in such a way as to surround the object under examination 1 if the static magnetic field generation system 2 is of the horizontal magnetic field type. On the other hand, the receiving-side high-frequency coil 14b is arranged in such a way as to face or surround the object under examination 1.

A current imaging target nuclear species for the MRI apparatus, which is in widespread clinical use, is a hydrogen nucleus (proton), which is a principal component material of the object under examination. Representing information about a spatial distribution of proton densities or a spatial distribution of relaxation times of excited states by an image enables performing two-dimensional or three-dimensional imaging of the morphology or function of, for example, the head region, abdominal region, or extremities of the human body.

<Capturing of Function Image>

Figure 2:
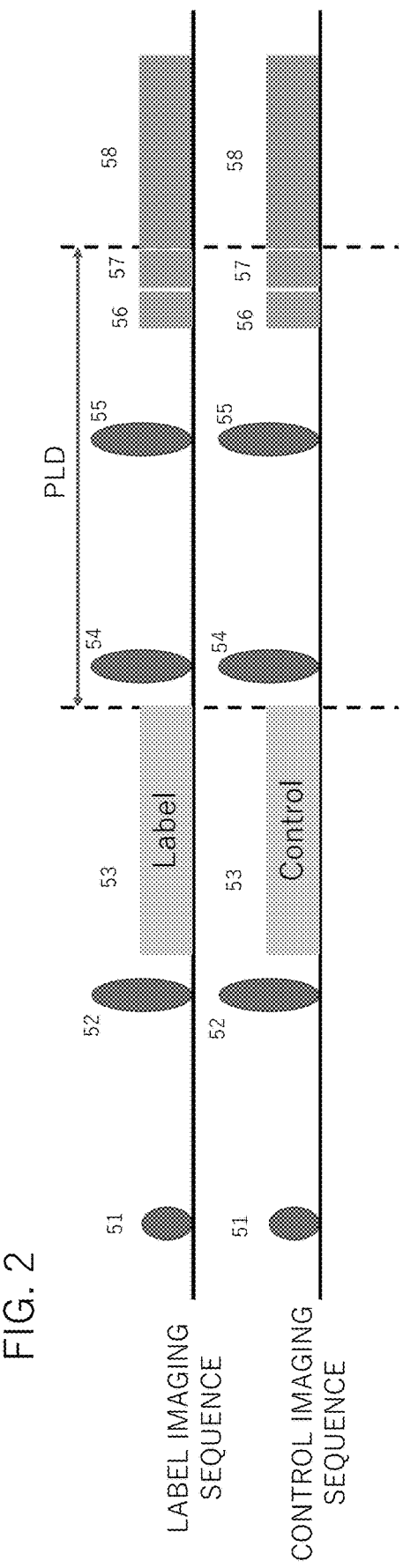
FIG. 2 is a diagram used to explain an example of an imaging pulse sequence in the ASL method.

The measurement control unit (sequencer) 4 captures, as a function image, an image of cerebral blood flow by the arterial spin labeling (ASL) method. FIG. 2 illustrates an example of an imaging sequence. Labeling methods for ASL include a pulsed ASL method and a pseudo-continuous ASL (pASL) method, and the sequence illustrated in FIG. 2 is an example of the sequence of the pASL method. The measurement control unit (sequencer) 4 performs the imaging sequence illustrated in FIG. 2 by controlling, for example, the gradient magnetic field generation unit 3, the irradiation coil 14a, and the receiving coil 14b. The ASL method performs labeling by radiating high-frequency pulses for inverting protons to the blood which passes through a label plane set on the more upstream side of blood flow than an imaging region while adjusting an RF pulse and a gradient magnetic field, and then captures an image (label image) at timing at which a post labeling delay time (delay time PLD) when the blood arrives at the imaging region has elapsed. Similarly, the ASL method captures an image (control image) with respect to the same imaging region without inverting blood protons. The ASL method represents blood flow information by an image by obtaining a difference between the label image and the control image.

In the sequence illustrated in FIG. 2, the pASL method performs labeling of the blood which passes through the label plane, and then, to wait a label blood to flow into a region of interest, performs imaging after waiting for the post labeling delay time (delay time PLD).

Specifically, as illustrated in FIG. 2, the measurement control unit (sequencer) 4 performs a label imaging sequence, which captures a label image, and a control imaging sequence, which captures a control image. Each of these sequences is a sequence which sequentially performs, for example, radiation and application of the following RF pulses 51 to 58 and gradient magnetic field pulses. First, while a pre-saturation pulse 51, which inclines spins by 90 degrees, is radiated onto the imaging region, a gradient magnetic field is applied to dephase transverse magnetization. Next, an IR pulse 52, which is an iteration recovery pulse, is selectively or non-selectively radiated onto the imaging region. Next, in the label imaging sequence, an ASL pulse 53, which inverts blood protons by 180 degrees, is selectively radiated onto the label plane (for example, a region at a distance of 1 centimeter (cm) to 2 cm from the lower end of the cerebellum). In the control imaging sequence, a pulse 53, which does not invert blood protons, is similarly radiated onto the label plane. Next, IR pulses 54 and 55, which are iteration recovery pulses, are selectively radiated onto the imaging region. Additionally, a fat suppression pulse 56 is radiated onto the imaging region, and, subsequently, a blood flow signal suppression pulse 57 is non-selectively radiated. At timing at which a predetermined delay time (PLD) has elapsed after the ASL pulse 53 is radiated onto the imaging region, readout processing 58 is performed, so that an NMR signal is acquired from the imaging region. In the readout processing 58, specifically, an RF pulse is radiated onto the imaging region, and, after spins are excited by this radiation, while a readout gradient magnetic field and a phase encode gradient magnetic field are applied, an NMR signal is acquired by the receiving coil 14b.

With this processing, in the label imaging sequence, an NMR signal in the imaging region which is in a state in which the blood subjected to labeling has arrived at the imaging region is acquired, and the computation processing unit 8 reconstructs a label image from the acquired NMR signal. Moreover, in the control imaging sequence, an NMR signal is acquired with respect to the same imaging region without labeling of blood being performed, and the computation processing unit 8 reconstructs a control image from the acquired NMR signal.

Moreover, the measurement control unit (sequencer) 4 repeatedly performs an imaging sequence while changing a delay time (PLD) (a time from the end of application of the ASL pulse 53 to the start of the readout processing 58) (i.e., the multi-PLD ASL method). With this processing, the computation processing unit 8 reconstructs a plurality of label images which are different in delay time (PLD).

The computation processing unit 8 calculates a cerebral blood flow (cerebral blood flow quantity, hereinafter referred to as "CBF") image and an arterial transit time (arterial blood flow arrival time, hereinafter referred to as "ATT") image from the obtained ASL image.

<Normalization of Function Image>

Next, the computation processing unit 8 applies anatomical normalization to the ATT image and the CBF image. Additionally, the computation processing unit 8 performs region of interest (ROI) analysis and voxel analysis on the anatomically normalized ATT image and CBF image, thus performing statistical analysis. With this processing, the computation processing unit 8 visualizes an abnormal blood flow from a result of the statistical analysis and displays the visualized abnormal blood flow.

<Control and Computation Processing Operations of Computation Processing Unit 8>

Figure 6:
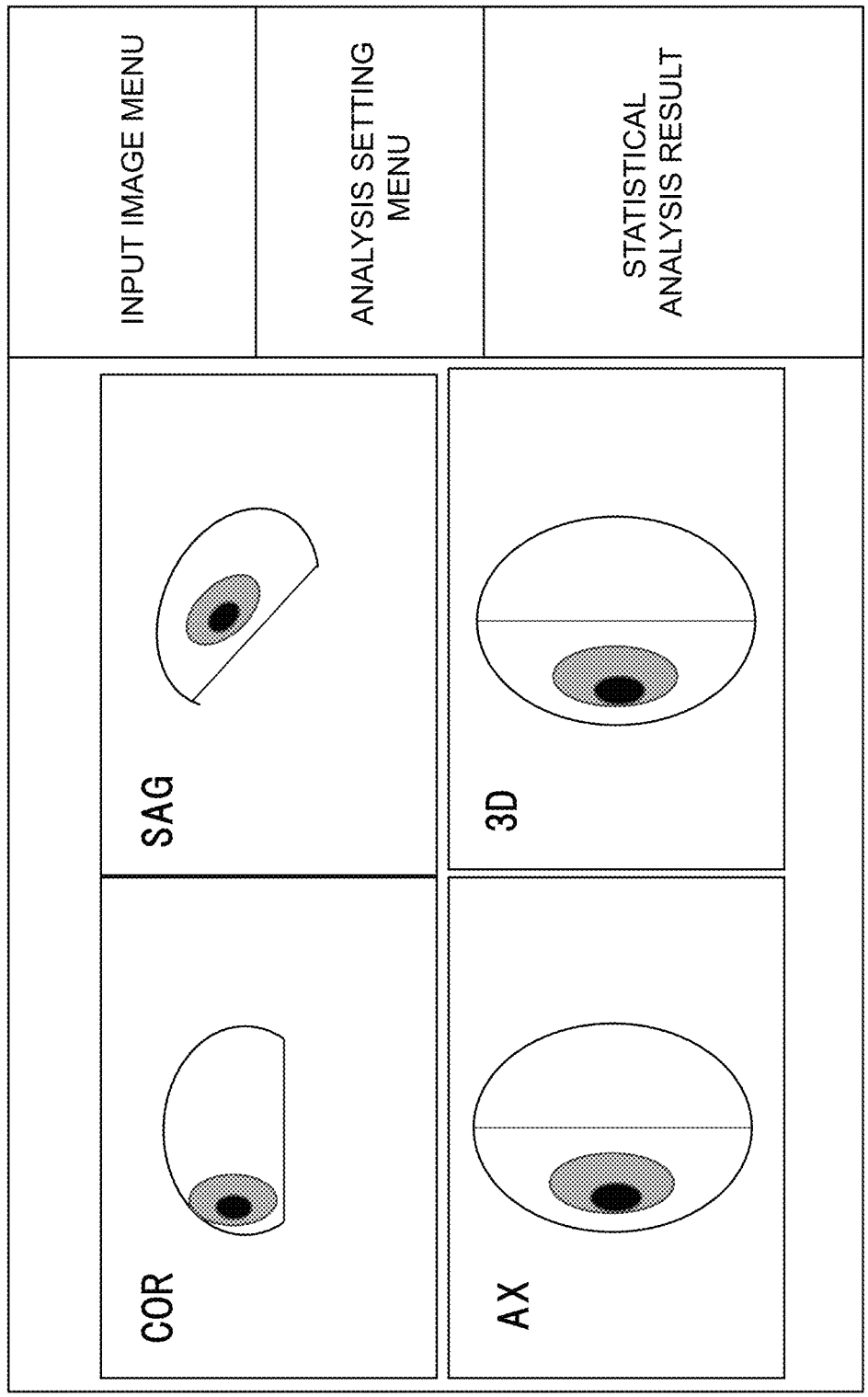
FIG. 6 is a diagram illustrating an example of a graphical user interface (GUI) showing, for example, images generated by the computation processing unit 8 of the MRI apparatus in the first embodiment and analysis results of the generated images.

Control and computation processing operations of the computation processing unit 8 are specifically described with reference to the flowchart of FIG. 3. FIG. 4 is a diagram illustrating an example of a scan condition (imaging condition), FIGS. 5A1, 5A2, 5A3, 5B1, and 5B2 illustrate images obtained in a process of the flow in the first embodiment, and FIG. 6 illustrates examples of images which display results of imaging in the first embodiment.

Figure 3:
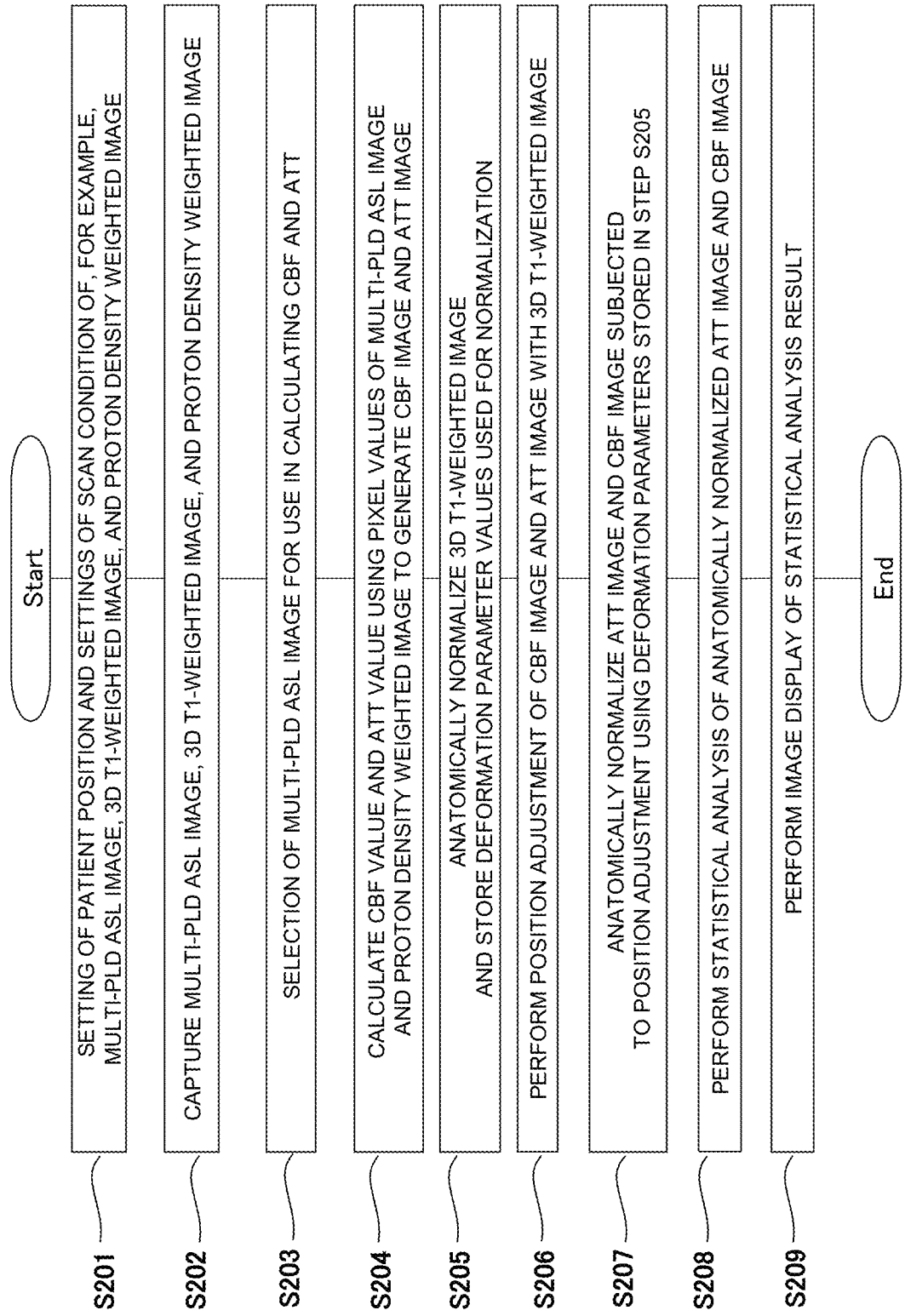
FIG. 3 is a flowchart illustrating a processing flow of a computation processing unit 8 of the MRI apparatus in the first embodiment.

Here, control and computation processing operations of the computation processing unit 8 in the flow illustrated in FIG. 3 are implemented in software by a CPU included in the computation processing unit 8 reading and executing a program previously stored in, for example, the magnetic disc 18. Furthermore, apart or the whole of the computation processing unit 8 can be implemented in hardware. For example, a part or the whole of the computation processing unit 8 can be configured with use of a custom integrated circuit (IC), such as an application specific integrated circuit (ASIC), or a programmable IC, such as a field-programmable gate array (FPGA), and circuit design can be performed in such a way as to implement functions of such an IC.

First, the operator mounts the object under examination 1 on a bed in the imaging region.

(Step S201)

The computation processing unit 8 receives settings of a scan condition for the imaging sequences of a multi-PLD ASL image, a 3D T1-weighted image, and a proton density weighted image from the user via the operation unit 25. For example, the computation processing unit 8 receives respective settings of the scan condition illustrated in FIG. 4. The imaging region is a whole brain region in each of the imaging sequences of a multi-PLD ASL image, a T1-weighted image, and a proton density weighted image. In the imaging sequence of a multi-PLD ASL image, here, seven types of times in the range of 500 milliseconds (ms) to 3000 ms are set as the delay time (PLD).

(Step S202)

The computation processing unit 8 instructs the measurement control unit (sequencer) 4 to perform a multi-PLD ASL imaging sequence illustrated in FIG. 2 on the scan condition set in step S201. In response to this instruction, the sequencer 4 controls, for example, the gradient magnetic field generation unit 3, the irradiation coil 14a, and the receiving coil 14b to perform an imaging sequence. The computation processing unit (CPU) 8 receives data from the reception system 6 and reconstructs an ASL image for each delay time (PLD) of multi-PLD of the above-mentioned imaging region.

Moreover, the computation processing unit 8 causes the sequencer (measurement control unit) 4 to perform, for example, a known gradient echo sequence before or after a multi-PLD ASL imaging sequence. With this processing, the computation processing unit (CPU) 8 receives data from the reception system 6 and reconstructs a 3D T1-weighted image in the above-mentioned imaging region. Additionally, the computation processing unit 8 captures a proton density weighted image in the above-mentioned imaging region using, for example, a known GRACE sequence, which is the same as the ASL imaging sequence. Furthermore, the imaging region, field of view (FOV), and Matrix of a proton density weighted image are set the same as those of ASL. In a case where they are different, for example, registration between an ASL image and a proton density weighted image can be performed after reconstruction.

The computation processing unit 8 stores each piece of reconstructed image data in the magnetic disc 18.

(Step S203)

The computation processing unit 8 receives selection of an ASL image of delay time (PLD) for use in calculating CBF and ATT from the operator via the operation unit 25. Furthermore, such selection of an ASL image can be configured to be automatically performed.

(Step S204)

The computation processing unit 8 calculates ATT and CBF for each pixel from pixel values of the multi-PLD ASL image selected in step S203 and thus generates an ATT image and a CBF image. For example, the computation processing unit 8 calculates, for each delay time (PLD), a theoretical value of the ASL signal using theoretical formulae that are based on two compartment models in formulae (1) and (2). The computation processing unit 8 fits changes of the theoretical value of the ASL signal caused by the delay time (PLD) to actual measured values of the ASL signal for each PLD (i.e., pixel values of an ASL image captured for each PLD) by, for example, curve fitting that is based on a non-linear least-square method, thus calculating ATT and CBF for each pixel. The computation processing unit 8 is able to generate, from an ATT value and a CBF value for each pixel, an ATT image, which display values of ATT as pixel values, and a CBF image, which displays values of CBF as pixel values. Furthermore, the methods for solving the theoretical formulae, i.e., formulae (1) and (2), are described as known methods in the above-mentioned Non-Patent Literature 1 and, therefore, the detailed description thereof is omitted here.

$$\frac{d(M_m(t))}{dt} = -(1/T_{1m}) * [M_m(t) - M_{m0}] - \quad (1)$$
$$k_{in}M_m(t) + (k_{out}/\lambda) * M_e(t) + (f/\lambda) * [M_a(t) - M_v(t)]$$

$$\frac{d(M_e(t))}{dt} = -(1/T_{1e}) * [M_e(t) - M_{e0}] + k_{in}\lambda M_m(t) - k_{out}M_e(t) \quad (2)$$

In formula (1), t denotes a time, and $T_{1m}$ is an intravascular apparent T1 value. $T_{1e}$ denotes an extravascular apparent T1 value. $M_o$ is a value expressed by using magnetization (pixel value) of a proton density weighted image, $M_{mo}$ denotes an intracapillary value of the proton density weighted image, and $M_{eo}$ denotes an extracapillary value of the proton density weighted image. The other variables and coefficients are as described in the following Table 1.

TABLE 1

| | |
|---|---|
| f | Blood flow |
| λ | Cerebral blood flow partition coefficient |
| $k_{in}$ | Transfer ratio of water from the microvascular to the extravascular space |
| $k_{out}$ | Transfer ratio of water from the extravascular to the microvascular space |
| $M_m$ (t) | Magnetization of microvascular water |
| $M_e$ (t) | Magnetization of extravascular water |
| $M_a$ (t) | Magnetization of arterial blood water |
| $M_v$ (t) | Magnetization of venous blood water |
| $M_0$ | The subscript of 0 denotes the equilibrium of magnetization. |

Furthermore, here, ATT and CBF are calculated by a non-linear least-square method that is based on two compartment models according to formulae (1) and (2), but can be calculated with use of known other theoretical formula models or fitting methods.
(Step S205)

The computation processing unit 8 performs processing for deforming the 3D T1-weighted image captured in step S202 to cause the deformed image to coincide with a standard brain (anatomical normalization), thus obtaining a deformation field for causing the 3D T1-weighted image to coincide with the standard brain.

Specifically, first, the computation processing unit 8 performs processing for moving the positions or shapes of structural objects (for example, gray matter or white matter) included in the 3D T1-weighted image to respective coordinates of predetermined structural objects of the standard brain using a known method, as illustrated in FIGS. 5A1 to 5A3 (anatomical normalization (standardization)). For example, the computation processing unit 8 performs normalization using diffeomorphic anatomical registration through exponentiated Lie algebra (DARTEL) processing, which performs non-linear conversion using a great number of parameters. The DARTEL processing deforms (anatomically normalizes) a structural object of a target brain according to a previously prepared standard brain template.

Next, the computation processing unit 8 stores, as deformation parameters, normalization parameters which have been used to deform the target brain (a set of values set to parameters of the DARTEL deformation formula).

Here, the method of acquiring anatomical normalization parameters can be not only the DARTEL processing but also another known normalization method.
(Step S206)

The computation processing unit 8 performs position adjustment (registration) to align the ATT image and the CBF image generated in step S204 with the 3D T1-weighted image captured in step S202, as illustrated in FIGS. 5B1 and 5B2. For example, the computation processing unit 8 performs position adjustment to align the ATT image and the CBF image with the 3D T1-weighted image using a known registration technique.

The position adjustment method to be used includes, for example, a method of calculating respective mutual information quantities MI between the ATT image and the 3D T1-weighted image and between the CBF image and the 3D T1-weighted image using the following formulae (3) to (6), and performs position adjustment in such a manner that the mutual information quantities MI become maximum (for example, performs rotational movement and translational movement thereof) is used.

$$MI(A, B) = \sum_{i=1}^{m} \sum_{j=1}^{n} p(a_i, b_j) \log_2 \frac{p(a_i, b_j)}{p(a_i)p(b_j)} \quad (3)$$

$$p(a_i, b_j) = \frac{h(a_i, b_j)}{\sum_{i=1}^{m} \sum_{j=1}^{n} h(a_i, b_j)} \quad (4)$$

$$p(a_i) = \sum_{j=1}^{n} p(a_i, b_j) \quad (5)$$

$$p(b_j) \sum_{i=1}^{n} p(a_i, b_j) \quad (6)$$

In formulae (3) to (6), ai denotes a pixel value (tone) of a given pixel of the ATT image or the CBF image, and bj denotes a pixel value (tone) of a corresponding pixel of the 3D T1-weighted image. h (ai,bj) denotes a two-dimensional histogram obtained by counting the frequencies of combinations of pixel values (tones) with respect to combinations (ai,bj) of pixel values of all of the corresponding pixels and performing mapping of the counted frequencies. p (ai,bj) denotes a probability at which pixel values ai and bj occur simultaneously (simultaneous probability), and is calculated by formula (4). p (ai) and p (bj) denote probabilities at which a pixel value ai and a pixel value bj respectively occur (marginal probability), and are calculated by formulae (5) and (6), respectively.
(Step S207)

The computation processing unit 8 respectively deforms the ATT image and the CBF image, which have been subjected to position adjustment in step S206, using values of the deformation parameters stored in step S205.

This enables performing anatomical normalization of ATT and CBF.

Furthermore, it is desirable that processing similar to that in step S205 be used for deformation processing, and, while, here, the DARTEL processing is used, different known deformation processing can be used.
(Step S208)

The computation processing unit 8 performs analysis of cerebral hemodynamics using the ATT image and CBF image anatomically normalized in step S207. For example, the computation processing unit 8 calculates how much the normalized ATT image and CBF image of the object under examination calculated in step S207 deviate from a healthy subject database (a database obtained by collecting anatomically normalized ATT images and CBF images of, for example, 50 healthy subjects). For example, the computation processing unit 8 calculates such a deviation as z-score for each voxel and thus calculates the degree of deviation (deviation degree) of the normalized ATT image and CBF image of the object under examination from a healthy subject image as a numerical value (z-score).

(Step S209)

The computation processing unit 8 displays, on the display 20, the degree of deviation (z-score) of the blood flow quantity (CBF image) and/or the blood flow arrival time (ATT image) calculated in step S208. The display screen displays, for example, cross-section images and three-dimensional (3D) images of the CBF image and the ATT image as illustrated in FIG. 6, and displays z-score in gray scale on the displayed images. The ATT image and/or the CBF image to be displayed can be a normalized image or can be an image obtained before being normalized. Furthermore, in the present embodiment, in FIG. 6, the degree of deviation (z-score) of the blood flow quantity (CBF image) and/or the blood flow arrival time (ATT image) is displayed in gray scale, but naturally can be displayed in color.

Thus far is the description of the processing flow of the computation processing unit 8 in the first embodiment.

As described above, in the first embodiment of the present invention, the computation processing unit 8 is able to calculate a function image (ATT image and CBF image), which does not include shape information about a brain, and then perform anatomical normalization. This enables performing voxel analysis with respect to the anatomically normalized function image (ATT image and CBF image) and thus performing, for example, statistical analysis. Therefore, it becomes possible to visualize an abnormal blood flow deviating from an image of the healthy subject based on a result of the statistical analysis and display the visualized abnormal blood flow, and it becomes possible to evaluate, with only an MRI apparatus, the cerebral blood flow quantity in, for example, dementia, cerebral vascular diseases, and epilepsy in which a decrease of cerebral blood flow is found.

Furthermore, while, in the above-mentioned step S203, selection of an image (multi-PLD ASL image) used for calculating a function image (ATT image and CBF image) is configured to be received from the user, the computation processing unit 8 can be configured to automatically perform such selection according to a predetermined criterion.

Moreover, a configuration in which the selected image is stored in, for example, the magnetic disc 18 in advance and step S204 and subsequent steps are performed at a later date can be employed.

Second Embodiment

An MRI apparatus in a second embodiment of the present invention is described.

As with the first embodiment, the MRI apparatus in the second embodiment calculates an ATT image and a CBF image and then applies anatomical normalization to the ATT image and the CBF image. The MRI apparatus in the second embodiment performs ROI analysis with respect to the anatomically normalized ATT image and CBF image and performs statistical analysis to visualize and display an abnormal blood flow.

Figure 7:
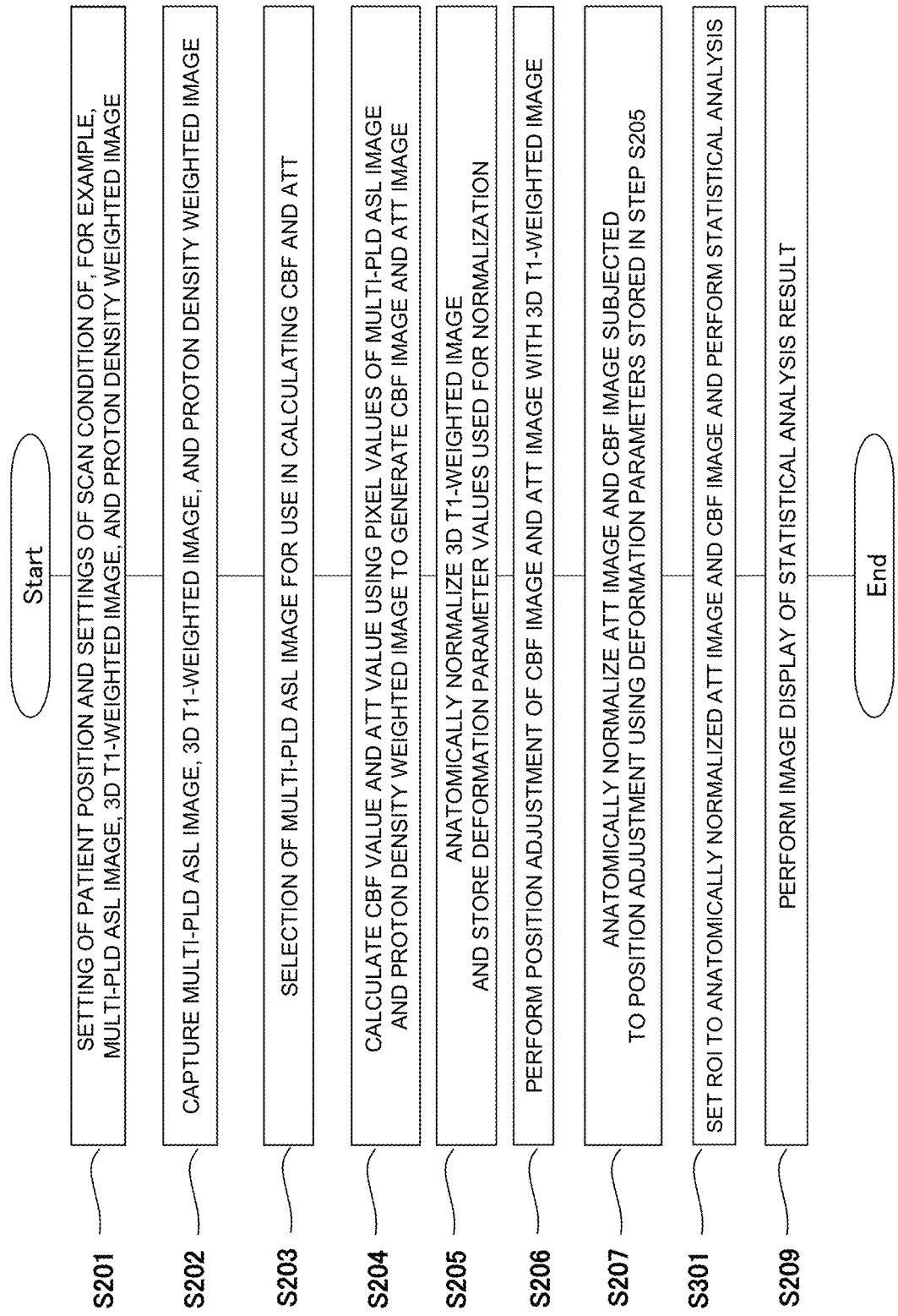
FIG. 7 is a flowchart illustrating a processing flow of the computation processing unit 8 of an MRI apparatus in a second embodiment.

FIG. 7 illustrates a processing flow of the computation processing unit 8 in the second embodiment. Processing which is performed by the computation processing unit 8 is described below with reference to FIG. 7. Furthermore, in the flow illustrated in FIG. 7, the same steps as those in the flow illustrated in FIG. 3 in the first embodiment are assigned the respective same step numbers, and the description thereof is omitted here.

(Steps S201 to S207)

The computation processing unit 8 performs steps S201 to S207 similar to steps S201 to S207 in the first embodiment to generate the anatomically normalized ATT image and CBF image.

(Step S301)

The computation processing unit 8 sets one or more regions of interest (ROIs) to the ATT image and CBF image anatomically normalized in step S207. The ROI can be the shape of a structural object of the standard brain, or can be an ROI of the desired shape drawn by the user. For example, an ROI of a known brain atlas such as an automated anatomical labeling (AAL) atlas can be selected, or an ROI can be, for example, drawn on an image by the user.

The computation processing unit 8 performs analysis of cerebral hemodynamics in an ROI of the anatomically normalized ATT image and CBF image. For example, the computation processing unit 8 calculates, as z-score for each ROI, the degree of deviation of the ATT image and the CBF image from the healthy subject database, and analyzes the degree of deviation of the blood flow arrival time and the blood flow quantity from those of a health subject. Specifically, for example, the computation processing unit 8 obtains z-score which indicates how much the blood flow arrival time or the blood flow quantity of an ROI of the object under examination deviates from the average value of the blood flow arrival times or the blood flow quantities of ROIs of 50 subjects in the healthy subject database. With this processing, in a case where there is a plurality of regions (ROIs), it is possible to calculate a value (z-score) which indicates the degree of deviation for each ROI.

(Step S209)

As with step S209 in the first embodiment, the computation processing unit 8 displays, on the display 20, the ATT image and/or the CBF image and z-score calculated for the ROI. For example, the computation processing unit 8 displays z-score in superimposition on the position of an ROI of the ATT image or the CBF image.

As described above, in the second embodiment of the present invention, since it is possible to calculate z-score from the result of statistical analysis and display the calculated z-score together with the ATT image and/or the CBF image, z-score is large. Thus, it is possible to visualize an ROI deviating from the image of a healthy subject and display the visualized ROI. With this processing, it becomes possible to evaluate, with only an MRI apparatus, the cerebral blood flow quantity in, for example, dementia, cerebral vascular diseases, and epilepsy in which a decrease of cerebral blood flow is found, as with the above-described first embodiment.

Moreover, in the second embodiment, since an ROI is set and the inside of the ROI is analyzed, it becomes possible to determine whether the blood flow in the ROI is lower than that of a healthy subject in a simple way and with a small amount of calculation.

Furthermore, while, in the present embodiment, an example in which, in step S301, a known ROI atlas such as an AAL atlas or an ROI drawn by the user is set as an ROI has been described, the computation processing unit 8 can be configured to set an ROI. For example, the computation processing unit 8 can be configured to previously extract a region having a significant difference in blood flow between a healthy subject database and a disease database and define the extracted region as an ROI and then set the defined ROI as an ROI in step S301.

Moreover, the computation processing unit 8 can be configured to compare the ATT image and/or the CBF image generated in step S207 with an image in the healthy subject database, extract a region having a significant difference, and set the extracted region as an Roi in step S301.

Third Embodiment

An MRI apparatus in a third embodiment is described.

The MRI apparatus in the third embodiment has the function of calculating a probability of an object under examination having a disease, with use of the ATT image and the CBF image.

Figure 8:
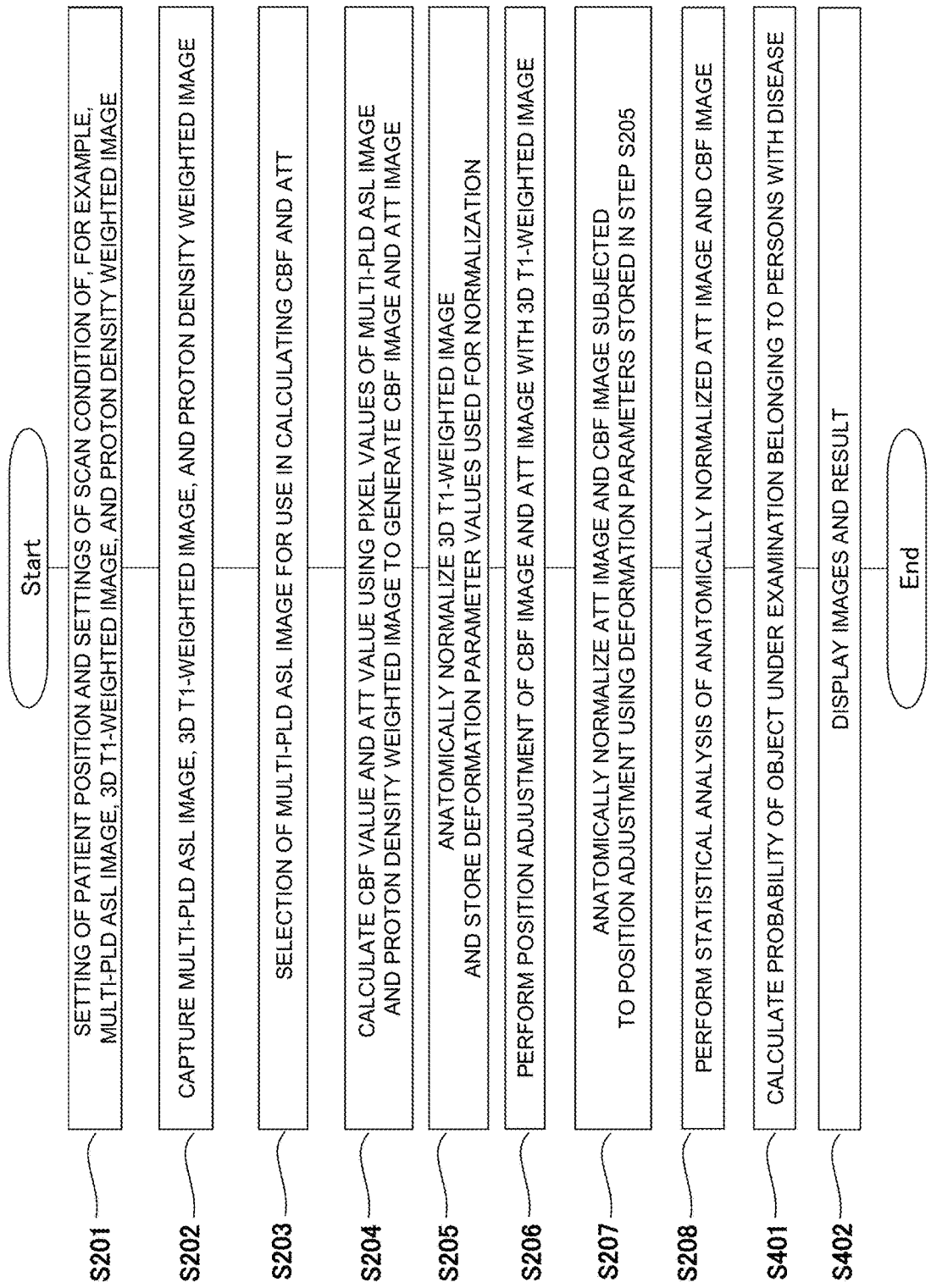
FIG. 8 is a flowchart illustrating a processing flow of the computation processing unit 8 of an MRI apparatus in a third embodiment.

FIG. 8 is a flowchart illustrating a processing flow of the computation processing unit 8 in the third embodiment. Steps illustrated in FIG. 8 are described as follows.

(Steps S201 to S208)

As with the first embodiment or the second embodiment, the computation processing unit 8 generates the anatomically normalized ATT image and CBF image.

(Step S401)

The computation processing unit 8 previously sets a predetermined ROI using, for example, a brain atlas to an ATT image and CBF image in a healthy subject database (a database obtained by collecting anatomically normalized ATT images and CBF images of healthy subjects) and a disease database (a database obtained by collecting anatomically normalized ATT images and CBF images of persons with disease) and obtains a feature quantity for each ROI. For example, the feature quantity to be used includes the average value of pixel values (ATT values or CBF values). The computation processing unit 8 previously obtains a boundary (discriminant plane) between the distribution of feature quantities of ATT images and CBF images of healthy subjects and the distribution of feature quantities of those of persons with disease. The method of obtaining a discriminant plane to be used includes a known method (for example, a machine learning algorithm such as a support vector machine).

The computation processing unit 8 sets the above-mentioned predetermined ROI to the normalized ATT image and CBF image of the object under examination obtained in step S207, calculates a feature quantity, calculates whether the calculated feature quantity is present on the side of a healthy subject or on the side of a person with disease with respect to the discriminant plane, and also calculates a distance of the calculated feature quantity from the discriminant plane. The computation processing unit 8 calculates a probability of the object under examination belonging to persons with disease by a known method based on the calculated distance.

(Step S402)

The computation processing unit 8 displays the normalized ATT image and CBF image and a result calculated in step S401 (the probability of the object under examination belonging to persons with disease). At this time, the computation processing unit 8 can display the distance calculated in step S401 together with the probability.

Thus far is the description of the processing flow of the computation processing unit 8 in the third embodiment.

The above-described MRI apparatus in the third embodiment is able to calculate a probability of an object under examination having a disease from the ATT image and the CBF image, and is, therefore, able to help a doctor make a diagnosis.

Furthermore, the method of calculating the above-mentioned discriminant plane (boundary) is not limited to a machine learning algorithm such as a support vector machine, but can be any method as long as being able to discriminate a similarity in ATT image and CBF image between a person with disease and a healthy subject. For example, the method of calculating the discriminant plane can be a deep learning method other than the support vector machine, a clustering method, or a statistical analysis method.

Fourth Embodiment

An MRI apparatus in a fourth embodiment is described.

The fourth embodiment is configured to perform analysis of blood flow using not a multi-PLD ASL image but a single PLD image (an image of blood flow quantity). Thus, the fourth embodiment is configured to calculate a CBF image from a single PLD image, perform anatomical normalization and statistical analysis in manners similar to those in the first and second embodiments, and display a result.

Figure 9:
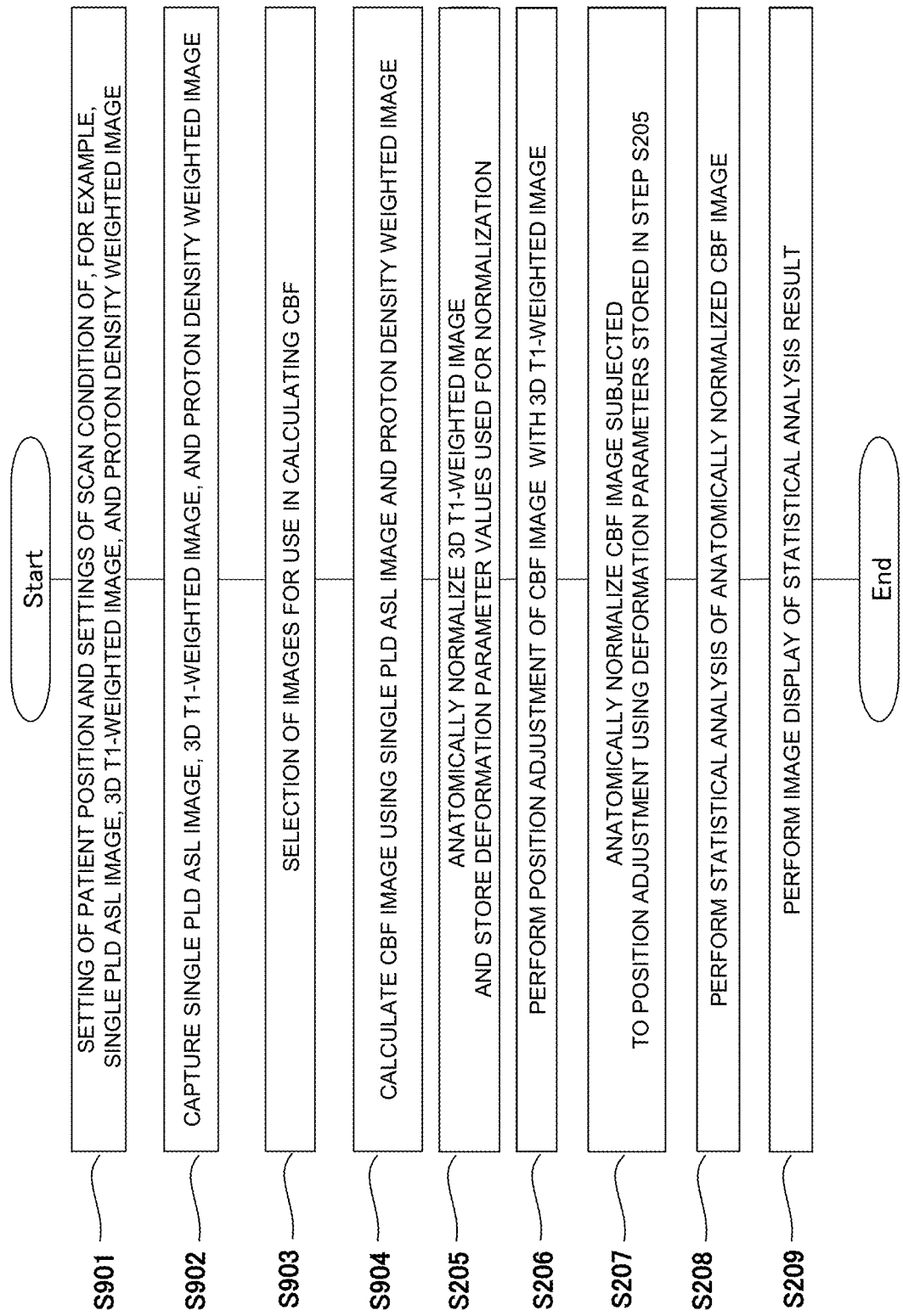
FIG. 9 is a flowchart illustrating a processing flow of the computation processing unit 8 of an MRI apparatus in a fourth embodiment.

FIG. 9 is a flowchart illustrating a processing flow of the computation processing unit 8 in the fourth embodiment of the present invention. Steps illustrated in FIG. 9 are described as follows. Furthermore, steps illustrated in FIG. 9 which are executed to perform processing operations similar to those in the steps illustrated in FIG. 3 are omitted from description here.

(Steps S901 to S903)

As with steps S201 to S202 illustrated in FIG. 3, the computation processing unit 8 receives settings of a scan condition from the user via the operation unit 25, and then performs a multi-PLD ASL imaging sequence illustrated in FIG. 2 in the first embodiment with single PLD (one delay time PLD) to capture a label image and a control image.

Moreover, the computation processing unit 8 captures a 3D T1-weighted image and a proton density weighted image.

The computation processing unit 8 selects, as images for use in calculating CBF, a label image and a control image captured with single PLD (one delay time PLD).

(Step S904)

The computation processing unit 8 calculates a CBF image from single PLD images and the proton density. The calculation method uses, for example, formula (7) to calculate CBF (f included in formula (7)) by assigning a difference $\Delta M$ in pixel value between the label image and the control image, a delay time PLD, and pixel values of the proton density (PD) to formula (7). The computation processing unit 8 generates a CBF image by calculating a CBF value for each pixel value.

$$\frac{\Delta M}{M_0} = \frac{2\alpha f T_{1a}}{\lambda}\left[1 - \exp\left(-\frac{\iota}{T_{1a}}\right)\right]\exp\left(-\frac{PLD}{T_{1a}}\right) \ (\delta_a < PLD) \quad (7)$$

$\Delta M$: the change in signal between the label image and control image $M_o$: the proton density image $\alpha$: the efficiency of inversion f: CBF $T_{1a}$: the arterial blood water relaxation time $\lambda$: the tissue blood partition coefficient of water τ: the duration of labeling
PLD: the post labeling delay
$\delta_\alpha$: the arterial transit time
(Steps S205 to S209)

As with steps S205 to S209 illustrated in FIG. 3 in the first embodiment, the computation processing unit 8 performs anatomical normalization to cause the 3D T1-weighted image to coincide with the standard brain, and anatomically normalizes the CBF image using deformation parameters used for the anatomical normalization. Then, the computation processing unit 8 calculates a degree of deviation (z-score) which indicates how much the normalized CBF image deviates from a CBF image in the healthy subject database. The computation processing unit 8 displays the calculated degree of deviation together with the CBF image.

Thus far is the description of the processing flow of the computation processing unit 8 in the fourth embodiment.

As described above, in the fourth embodiment of the present invention, it is possible to perform analysis of hemodynamics (CBF) using single PLD CBF. Therefore, even in a case where it is difficult to capture a multi-PLD ASL image, according to the fourth embodiment, it becomes possible to analyze hemodynamics using a single PLD ASL image.

Fifth Embodiment

An MRI apparatus in a fifth embodiment is described.

The fifth embodiment is configured to perform analysis in an individual brain space by deforming the ROI shape of a brain atlas in such a way as to cause the ROI shape to coincide with the brain morphology of an individual (object under examination). Thus, the fifth embodiment is configured not to deform the ATT image or the CBF image using deformation parameters in such a way as to cause the deformed image to coincide with the standard brain as in the first to fourth embodiments but to deform a brain atlas in such a way as to coordinate with the individual brain space of an object under examination by applying deformation parameters to the brain atlas in the opposite direction, and then to perform analysis of the ATT image or the CBF image using an ROI of the deformed brain atlas.

FIG. 10 is a flowchart illustrating a processing flow of the computation processing unit 8 in the fifth embodiment of the present invention. Steps illustrated in FIG. 10 are described in detail as follows.
(Steps S201 to S205)

The computation processing unit 8 executes steps S201 to S205 as with the first embodiment.
(Step S601)

The computation processing unit 8 deforms a brain atlas in the opposite direction using the deformation parameters stored in step S205. With this processing, the brain atlas is deformed into a shape which coincides with a 3D T1-weighted image of the object under examination obtained before being normalized.

Additionally, the computation processing unit 8 performs registration of the brain atlas deformed in the opposite direction with the ATT image and the CBF image. The method for deformation to be used includes, for example, a DARTEL method.
(Step S602)

The computation processing unit 8 calculates the degree of deviation from a healthy subject, as with step S208, using the brain atlas caused to coincide with the brain space of the object under examination calculated in step S601, the ATT image, and the CBF image.

(Step S209)

The computation processing unit 8 displays the degree of deviation, the ATT image, and the CBF image as with step S209 in the first embodiment.

Thus far is the description of the processing flow of the computation processing unit 8 in the fifth embodiment.

As described above, the fifth embodiment of the present invention is configured to perform analysis of cerebral hemodynamics by deforming an atlas in the opposite direction. It is possible to avoid changing of a value caused by deforming CBF and ATT with respect to the standard brain, and it becomes possible to perform more accurate blood flow evaluation.

Sixth Embodiment

An MRI apparatus in a sixth embodiment is described.

The sixth embodiment is configured to perform statistical analysis using a quantitative susceptibility mapping (QSM) image in addition to the ATT image, the CBF image, and the 3D T1-weighted image.

FIG. 11 is a flowchart illustrating a processing flow of the computation processing unit 8 in the sixth embodiment of the present invention. Steps illustrated in FIG. 11 are described in detail as follows.
(Steps S1101 to S1102)

The computation processing unit 8 receives settings of a scan condition for a multi-PLD ASL image, a 3D T1-weighted image, and a proton density weighted image and performs imaging, as with steps S201 to S202 in the first embodiment, and, in the present embodiment, in addition to these, also receives settings of a scan condition for a QSM image and performs imaging.
(Steps S203 to S205)

The computation processing unit 8 executes steps S203 to S205 in the first embodiment to generate a CBF image and an ATT image and obtain deformation parameters for causing the 3D T1-weighted image to coincide with the standard brain.
(Step S1106)

The computation processing unit 8 performs analysis of QSM. For example, the computation processing unit 8 uses a known method to prepare a total magnetic field map obtained by eliminating phase aliasing from collected phase images, and further acquires a local magnetic field map obtained by eliminating a background magnetic field. On the other hand, the computation processing unit 8 acquires a magnetic susceptibility map (QSM) by estimating a dipole magnetic field.
(Steps S1107 to S1109)

The computation processing unit 8 performs position adjustment of the QSM image, in addition to the CBF image and the ATT image, with the 3D T1-weighted image as with steps S206 to S208 in the first embodiment, and then deforms these images using the deformation parameters stored in step S205 to perform anatomical normalization.

Additionally, the computation processing unit 8 performs statistical analysis using the anatomically normalized ATT image, CBF image, QSM image, and 3D T1-weighted image. For example, the computation processing unit 8 calculates the degree of deviation from the image of a healthy subject as with the first embodiment.

The computation processing unit 8 can be configured to perform analysis using, in addition to the ATT image and the CBF image, a plurality of image types such as the QSM image and the 3D T1-weighted image and to simultaneously calculate the degree of deviation in blood flow, the degree of deviation in magnetic susceptibility, and the degree of deviation in brain volume in the same region.

(Step S209)

The computation processing unit 8 performs image display of an analysis result.

Thus far is the description of the processing flow of the computation processing unit 8 in the sixth embodiment.

As described above, in the sixth embodiment of the present invention, it becomes possible to simultaneously calculate the degree of deviation in blood flow, the degree of deviation in magnetic susceptibility, and the degree of deviation in brain volume in the same region by performing analysis using a plurality of image types. Simultaneously analyzing the blood flow, magnetic susceptibility, and brain volume enables facilitating a diagnosis.

While the first to sixth embodiments of the present invention have been described above, the present invention is not limited to these embodiments.

Description of Reference Numerals

1: object under examination, 2: static magnetic field generation system, 3: gradient magnetic field generation system, 4: sequencer, 5: transmission system, 6: reception system, 7: signal processing system, 8: computation processing unit (CPU), 9: gradient magnetic field coil, 10: gradient magnetic field power source, 11: high-frequency oscillator, 12: modulator, 13: high-frequency amplifier, 14*a*: high-frequency coil (transmitting coil), 14*b*: high-frequency coil (receiving coil), 15: signal amplifier, 16: quadrature phase detector, 17: A/D converter, 18: magnetic disc, 19: optical disc, 20: display, 21: ROM, 22: RAM, 23: trackball or mouse, 24: keyboard.

What is claimed is:

1. A magnetic resonance imaging apparatus comprising:
    a static magnetic field generation unit that applies a static magnetic field to an imaging space in which an object under examination is placed;
    a gradient magnetic field generation unit that applies a gradient magnetic field to the imaging space;
    a transmitting coil that transmits a high-frequency magnetic field to the object under examination in the imaging space;
    a receiving coil that receives a nuclear magnetic resonance signal from the object under examination;
    a sequencer that performs an imaging sequence by controlling the gradient magnetic field generation unit, the transmitting coil, and the receiving coil to capture an image; and
    a computation processing unit coupled to a memory,
    wherein the sequencer captures, with respect to an equal imaging region of the object under examination, a morphology image with a morphology expressed therein and a function image with a function expressed therein, and
    wherein the memory stores instructions that when executed by the computation processing unit causes the computation processing unit to:
    execute processing for deforming the morphology image using a deformation parameter to move positions of one or more structural objects included in the morphology image to respective positions of structural objects of a previously determined standard morphology thereby causing the morphology image to coincide with the standard morphology by performing normalization using non-linear conversion using at least the deformation parameter, and
    then to execute processing for deforming the function image using a value of the deformation parameter used in deforming the morphology image to cause a position of a region included in the function image to coincide with a position of a corresponding region of the standard morphology or processing for deforming the standard morphology in an opposite direction using the value of the deformation parameter to cause a position of a region of the structural object of the standard morphology to coincide with a position of a corresponding region included in the function image,
    wherein the imaging sequence is a sequence which implements a post labeling delay (PLD) according to a single PLD arterial spin labeling (ASL) method of setting one type of time required from start of labeling of blood to execution of imaging and performing imaging using the one type of time, and
    wherein the function image is an image of cerebral blood flow (CBF).

2. The magnetic resonance imaging apparatus according to claim 1,
    wherein, before deforming the function image, the computation processing unit executes processing for causing a position of a region included in the function image to coincide with a position of a corresponding region of the morphology image.

3. The magnetic resonance imaging apparatus according to claim 1,
    wherein the standard morphology is a standard brain.

4. The magnetic resonance imaging apparatus according to claim 1,
    wherein the morphology image is a T1-weighted image.

5. A magnetic resonance imaging apparatus, comprising:
    a static magnetic field generation unit that applies a static magnetic field to an imaging space in which an object under examination is placed;
    a gradient magnetic field generation unit that applies a gradient magnetic field to the imaging space;
    a transmitting coil that transmits a high-frequency magnetic field to the object under examination in the imaging space;
    a receiving coil that receives a nuclear magnetic resonance signal from the object under examination;
    a sequencer that performs an imaging sequence by controlling the gradient magnetic field generation unit, the transmitting coil, and the receiving coil to capture an image; and
    a computation processing unit coupled to a memory,
    wherein the sequencer captures, with respect to an equal imaging region of the object under examination, a morphology image with a morphology expressed therein and a function image with a function expressed therein, and
    wherein the memory stores instructions that when executed by the computation processing unit causes the computation processing unit to:
    execute processing for deforming the morphology image using a deformation parameter to move positions of one or more structural objects included in the morphology image to respective positions of structural objects of a previously determined standard morphology thereby causing the morphology image to coincide with the standard morphology by performing normalization using non-linear conversion using at least the deformation parameter, and
    then to execute processing for deforming the function image using a value of the deformation parameter used in deforming the morphology image to cause a position of a region included in the function image to coincide with a position of a corresponding region of the standard morphology or processing for deforming the standard morphology in an opposite direction using the value of the deformation parameter to cause a position of a region of the structural object of the standard morphology to coincide with a position of a corresponding region included in the function image, wherein the function image is a cerebral blood flow image, wherein the standard morphology is a standard brain, and wherein the imaging sequence is a sequence which implements a post labeling delay (PLD) according to a multi-PLD arterial spin labeling (ASL) method of setting a plurality of types of times required from start of labeling of blood to execution of imaging and performing imaging using each of the plurality of types of times.

6. The magnetic resonance imaging apparatus according to claim 5, wherein the function image is an image of at least one of arterial transit time (ATT) and image of cerebral blood flow (CBF).

7. The magnetic resonance imaging apparatus according to claim 1, wherein the computation processing unit executes calculating a degree of deviation of the deformed function image of the object under examination from a healthy function image obtained by deforming a function image previously obtained about a healthy subject in such a way as to cause the previously obtained function image to coincide with a position of a corresponding region of the standard morphology.

8. The magnetic resonance imaging apparatus according to claim 7, wherein the computation processing unit executes setting a region of interest to the deformed function image of the object under examination, calculates a degree of deviation of the function image included in the region of interest from a corresponding region of the healthy function image, and displays the calculated degree of deviation to a user.

9. The magnetic resonance imaging apparatus according to claim 1, wherein the computation processing unit executes setting a region of interest to the deformed function image, calculates a feature quantity previously determined about the function image included in the region of interest, calculates on which side of a previously obtained boundary between a distribution of the feature quantities of a plurality of healthy subjects and a distribution of the feature quantities of a plurality of persons with disease the calculated feature quantity is present, and calculates a distance of the calculated feature quantity from the boundary.

10. The magnetic resonance imaging apparatus according to claim 1, wherein the function image includes a cerebral blood flow image and a quantitative magnetic susceptibility mapping image and the morphology image is a T1-weighted image, and wherein the computation processing unit executes calculating degrees of deviation of the cerebral blood flow image, the quantitative magnetic susceptibility mapping image, and an image included in a corresponding region of the T1-weighted image about the object under examination from the cerebral blood flow image, the quantitative magnetic susceptibility mapping image, and an image included in a corresponding region of the T1-weighted image about a healthy subject.

11. An image processing apparatus comprising:

a computation processing unit coupled to memory that receives, from a magnetic resonance imaging apparatus, the magnetic resonance imaging apparatus including a static magnetic field generation unit that applies a static magnetic field to an imaging space in which an object under examination is placed;

a gradient magnetic field generation unit that applies a gradient magnetic field to the imaging space;

a transmitting coil that transmits a high-frequency magnetic field to the object under examination in the imaging space;

a receiving coil that receives a nuclear magnetic resonance signal from the object under examination; and a sequencer that performs an imaging sequence by controlling the gradient magnetic field generation unit, the transmitting coil, and the receiving coil to capture an image, a morphology image with a morphology expressed therein and a function image with a function expressed therein captured with respect to an equal imaging region of an object under examination, wherein, the memory stores instructions that when executed by the computation processing unit causes the computation processing unit to execute processing for:

deforming the morphology image using a deformation parameter and to move positions of one or more structural objects included in the morphology image to respective positions of structural objects of a previously determined standard morphology thereby causing the morphology image to coincide with the standard morphology by performing normalization using non-linear conversion using at least the deformation parameter, and then deforming the function image using a value of the deformation parameter to cause a position of a region included in the function image to coincide with a position of a corresponding region of the standard morphology or processing for deforming the standard morphology in an opposite direction using the value of the deformation parameter to cause a position of a region of the structural object of the standard morphology to coincide with a position of a corresponding region included in the function image, wherein the imaging sequence is a sequence which implements a post labeling delay (PLD) according to a single PLD arterial spin labeling (ASL) method of setting one type of time required from start of labeling of blood to execution of imaging and performing imaging using the one type of time, and wherein the function image is an image of cerebral blood flow (CBF).

12. An image processing method comprising:

capturing a morphology image with a morphology expressed therein and a function image with a function expressed therein captured with respect to an equal imaging region of an object under examination obtained by a magnetic resonance imaging apparatus, the magnetic resonance imaging apparatus including a static magnetic field generation unit that applies a static magnetic field to an imaging space in which an object under examination is placed;

a gradient magnetic field generation unit that applies a gradient magnetic field to the imaging space;

a transmitting coil that transmits a high-frequency magnetic field to the object under examination in the imaging space;

a receiving coil that receives a nuclear magnetic resonance signal from the object under examination; and a sequencer that performs an imaging sequence by controlling the gradient magnetic field generation unit, the transmitting coil, and the receiving coil to capture an image;

deforming the morphology image using a deformation parameter to move positions of one or more structural objects included in the morphology image to respective positions of structural objects of a previously determined standard morphology thereby causing the morphology image to coincide with the standard morphology by performing normalization using non-linear conversion using at least the deformation parameter; and deforming the function image using a value of the deformation parameter to cause a position of a region included in the function image to coincide with a position of a corresponding region of the standard morphology or deforming the standard morphology in an opposite direction using the value of the deformation parameter to cause a position of a region of the structural object of the standard morphology to coincide with a position of a corresponding region included in the function image, wherein the imaging sequence is a sequence which implements a post labeling delay (PLD) according to a single PLD arterial spin labeling (ASL) method of setting one type of time required from start of labeling of blood to execution of imaging and performing imaging using the one type of time, and wherein the function image is an image of cerebral blood flow (CBF).

* * * * *